United States Patent [19]

Sustmann et al.

[11] Patent Number: 4,634,438

[45] Date of Patent: Jan. 6, 1987

[54] PH-REGULATING CELLULOSE PRODUCTS

[75] Inventors: Scarlet Sustmann, Viersen, Fed. Rep. of Germany; Ingo G. Marini, Lenzing, Austria

[73] Assignee: Henkel Kommanditgesellschaft auf Aktien, Dusseldorf, Fed. Rep. of Germany

[21] Appl. No.: 660,334

[22] Filed: Oct. 12, 1984

[30] Foreign Application Priority Data

Oct. 14, 1983 [DE] Fed. Rep. of Germany ....... 3337444

[51] Int. Cl.⁴ ...................... A61F 13/16; A61F 13/20; B01J 20/24; B01J 20/28
[52] U.S. Cl. .................................... 604/376; 604/904; 536/87; 536/89; 424/28; 128/155; 128/158; 128/127; 128/132 R; 106/169
[58] Field of Search ............... 604/376, 358, 285, 904; 128/155, 158, 127, 132 R; 106/169; 536/87, 88, 89; 424/28

[56] References Cited

U.S. PATENT DOCUMENTS

| | | | |
|---|---|---|---|
| 3,067,745 | 12/1962 | Burgeni et al. | 604/376 |
| 3,187,747 | 6/1965 | Burgeni | 128/156 |
| 4,044,766 | 8/1977 | Kaczmarzyk et al. | 128/283 |
| 4,405,324 | 9/1983 | Cruz, Jr. | 603/376 |
| 4,431,427 | 2/1984 | Lefren et al. | 604/285 |

FOREIGN PATENT DOCUMENTS 2309575 9/1974 Fed. Rep. of Germany .

Primary Examiner—Harold D. Anderson
Assistant Examiner—Nathan M. Nutter
Attorney, Agent, or Firm—Ernest G. Szoke; Mark A. Greenfield

[57] ABSTRACT

Hygienic products of various types, all comprising as their operative body contact portion a fiber mass of acidic, modified, pH-regulating, cellulose.

13 Claims, No Drawings

PH-REGULATING CELLULOSE PRODUCTS

BACKGROUND OF THE INVENTION

1. Field of the Invention

This invention relates to products manufactured from pH-regulating chemically modified cellulose fibers.

2. Statement of the Related Art

Absorbent materials, particularly those for medical, hygienic, and cosmetic use such as catamenial devices, bandaging, shoe insole pads, and the like, usually consist of hydrophilic cotton linters, viscose fibers, flexible foams, etc.

Where such materials come into direct contact with parts of the body, it is advantageous to provide them with additives which positively affect the pH of the body at the point of contact, particularly by lowering or maintaining it. This assists in preventing irritation and reduces susceptibility to diseases, particularly those caused by alkaliphilic microorganisms.

An example of a known material of this type is disclosed in German Patent Application No. 23 09 575 which proposes impregnating tampons with substances which maintain a vaginal acid pH, such as glycogen, sugar, Doederlein bacteria, all of which help form lactic acid through Lactobacillus acidophilus. However, additives such as the above are not effective for their intended purpose, since the alkaline environment of the vagina during menstruation seriously inhibits the growth of L. acidophilus.

It has also been proposed in German Patent Application No. 23 09 575 (above) to impregnate with lactic acid per se, as well as citric acid, and the like. However, because of the strong buffer effect of menstrual fluid, and because of the relatively small amount of acid with which a tampon may be impregnated, the beneficial effect of the impregnant is exhausted after only a small accumulation of menstrual blood.

U.S. Pat. No. 4,431,427 and corresponding German Patent Application No. 32 36 768 describe tampons containing one or more substances which, when the tampon is in use, produce and maintain a pH in the range 2.5 to 4.5 and thus prevent the growth of pathogenic bacteria. Substances of the type in question are disclosed as including monomeric and/or polymeric, physiologically compatible carboxylic acids, such as citric acid, malic acid, tartaric acid or lactic acid. Tampons of this type also have the disadvantage that the strong buffer effect of the body fluids limits the acidifying effect of the acids introduced into the tampon.

U.S. Pat. No. 3,187,747 describes absorbing fiber materials having ion-exchange properties where the composition is a multicomponent polymer system. Polymer components having fiber-forming properties, for example textile fibers, are present alongside other polymers having acidifying properties, for example carboxymethyl cellulose, in the form of "polymer alloys" which may be obtained from homogeneous solutions of suitable polymers. The heterogeneity of the starting polymers means that the processing of the polymer alloys into the required hygiene aids involves additional process steps, such as solvent exchange drying, in order to degelatinize the fibers and to prevent them from sticking to one another during the drying process. In addition, fibers of the type in question are frequently treated with cation-active softeners and lubricants to improve their processing properties, although this adversely affects the acidifying properties of the fiber material.

Another process in which a known material, a modified viscose fiber, is blended with a substance which, in use, produces a reduction in the pH is described in U.S. Pat. No. 4,044,766 and corresponding German Patent Application No. 27 09 132. Cellulose fibers are reacted with monochloroacetic acid to form carboxymethyl cellulose. The resulting carboxymethyl cellulose fibers have an average degree of substitution of from 0.4 to 2.0. This etherification process is carried out on the "finished" fiber. The disadvantage of this known process is that the subsequent etherification step yields fibers having a slimy surface which are unsuitable for medical, cosmetic, or similar applications. In addition, materials produced from fibers of this type only contain free carboxyl groups at the fiber surface, with the result that cationic substances present in body fluids bring about a rapid and complete deactivation of the pH-regulating capabilities of the fiber surface.

DESCRIPTION OF THE INVENTION

This invention affords particularly useful products for medical, hygienic and cosmetic use, all of which employ a novel homogeneous cellulose fiber which has been chemically modified to be effective as a pH-regulator.

Description of the fiber

The products of this invention employ fiber masses made from a homogeneous plurality of modified carboxyalkylated (viscose) fibers characterized by a degree of substitution of about 0.01 to 0.3 (preferably about 0.07 to 0.1) which corresponds to about 1 to 30 (preferably about 7 to 10) carboxyalkyl groups per 100 anhydroglucose units, wherein substantially all of the carboxyalkyl groups are in the free acid form. This material demonstrates hardly any difference from conventional, unmodified, fibers both in its processing properties and in its service properties. For example, fiber masses of this material have a high absorption capacity which make it suitable for all normal absorbent cotton uses in addition to its novel and highly desirable pH-regulating capacity.

Most importantly, the carboxyalkyl groups are distributed throughout the novel fiber, as contrasted with prior art fibers in which the substituted groups are mostly on the fiber surface. It is believed that this distribution of the carboxyalkyl groups makes the fiber mass material particularly effective for reasons that will be discussed below.

The alkyl moiety may have 1 to 3 carbon atoms, methyl being preferred. When the alkyl is methyl, the carboxyalkyl group content (COOH % by weight) of the cellulose fiber should be about 1.9 to 2.7 % by weight, most preferably about 2 % by weight of the total fiber weight. This may be contrasted with a normal viscose fiber, which would contain about 0.3 % by weight of carboxyl groups. The percentage will be fractionally lower if the alkyl has more than 1 carbon atom.

As a result of the coupled free acid moieties, the fiber mass used in this invention has a pH of between about 3 and 4, most preferably about 3.4 to 3.9, when determined by Deutsche Industrienorm (DIN) 54,275. It will maintain in use a pH below about 6, preferably about 4 to 5 in tampons. The pH may vary depending upon the degree of carboxyalkyl substitution, and may be considered as an independent measurement of the number of free acid groups in the fiber.

The modified cellulose fibers are preferably prepared by first etherifying the cellulose polymer in a known manner, second preparing fibers from the etherified (i.e. carboxyalkylated) polymer mass, and third converting the alkalized carboxyalkyl fibers so that substantially all carboxy groups are in their free acid form, i.e. the carboxyalkyl groups consist essentially of carboxyalkyl groups in the free acid form. This sequence should be contrasted with the prior art process in which the fiber is first formed and then etherified [see comments regarding U.S. Pat. No. 4,044,766, above], which results in free carboxyl groups only at the fiber surface.

Carboxyalkylated cellulose fibers are already known, in which the carboxylation takes place before the fiber is formed. Such fibers are available, among others, from Chemiefaser Lenzing AG under the VISCOSORB trademark. In particular, fiber masses identified as VISCOSORB 1S and VISCOSORB 1N, are most useful for the purposes of this invention.

Fibers which were carboxylated prior to fiber forming are treated with at least one aqueous mineral acid at room temperature for a period of about 20 to 40 (preferably about 30) minutes. All acid that has not reacted with the carboxyalkyl groups to convert them to free acid form is then thoroughly removed.

The aqueous mineral acid may be dilute hydrochloric, sulfuric, or the like. Aqueous hydrochloric acid in a concentration of about 0.1 to 1% by weight (preferably about 0.2% by weight) is particularly useful.

The removal of all unreacted acid is particularly important, and may be accomplished by at least one cycle of washing with deionized water and expressing most of the water, ultimately followed by drying, preferably at a temperature of about 90° to 115° C., most preferably about 100° to 105° C.

It has been noted that the acidification treatment in the preferred process is conducted after the fiber has been formed.

The fiber masses used have a number of advantages over conventional, superabsorbent cotton wool.

Because of the low degree of substitution after conversion of the carboxylate group into the free acid form, the absorption capacity and absorption power of the materials used in this invention correspond to those of normal raw or regenerated cellulose or cotton.

Since the modification, i.e. etherification, is carried out on the actual cellulose raw material before production of the fiber, so that the free carboxyl groups are distributed throughout the fiber cross-section, the pH-regulating materials have a distinctly better buffer capacity than materials modified after production of the fiber. They are thus able not only to establish, but importantly also to maintain an acidic pH.

There are no additional process steps, (such as solvent exchange drying), necessitated by a fiber material consisting of two or more polymer components. The modified pH-regulating materials show the properties indicated in the following examples without the addition of any other components, such as softeners or lubricants. Accordingly, the disadvantages normally produced by additions of components such as these do not arise.

Production and properties of fiber/fiber masses useful in the products of this invention are demonstrated in the following Examples 1-3 and Tables 1-3.

EXAMPLE 1

Production of acidic fiber mass and determination of the fiber pH.

The fiber masses for the pH-regulating materials useful in this invention were produced by converting the carboxylate groups of commercially available alkalized carboxyalkyl cellulose produced from carboxyalkylated cellulose by the viscose process into the free acid form. Fiber masses in 1 kg quantity were treated for 30 minutes at room temperature with 20 liters of 0.2% hydrochloric acid. The material was then squeezed out to a moisture content of 200% and washed with fully deionized water until the washing water showed a neutral reaction. It was then squeezed out again to a moisture content of approximately 200% and dried for 4 hours at 105° C. in a recirculating air drying cabinet. Determination of the fiber pH by the extrapolation process according to DIN 54 275 produced the results listed in Table 1.

TABLE 1

| Determination of the fiber pH in accordance with DIN 54 275. | | |
|---|---|---|
| Fiber material | Carboxyl groups | Fiber pH |
| VISCOSORB 1N* | 1.9% by weight | 3.4 |
| VISCOSORB 1S* | 2.7% by weight | 3.0 |
| Normal viscose | 0.3% by weight | 6.5 |

*modified according to this invention

EXAMPLE 2

Liquid retention capacity using water and blood serum as the test liquids.

Determination of the liquid retention capacity of the materials useful in this invention was carried out with water in accordance with DIN 53 814 and with blood serum by the same method, but without the addition of wetting agents. The results are set out in Table 2 below.

TABLE 2

| Liquid retention capacity according to DIN 53 814. | | |
|---|---|---|
| Fiber Mass (% moisture after conditioning at 20° C./65% relative air humidity) | Retention capacity for: | |
| | Water (%) | Serum (%) |
| DANUFIL - a Hoechst product (14.3) | 65.2 | 70.1 |
| VISCOSORB 1N*- a Chemifaser Lenzing product (17.8) | 54.3 | 69.6 |
| VISCOSORB 1S*- a Chemifaser Lenzing product (16.9) | 53.3 | 70.9 |

*modified according to this invention

As can be seen, in the test carried out with blood serum, no differences were observed between the various materials. With water as the test liquid, the materials according to the invention show a slightly lower, but completely acceptable, retention capacity.

EXAMPLE 3

In vitro test for influencing the pH of blood serum by the materials according to the invention.

Quantities of 3.0 g of various fiber masses were added to quantities of from 10 to 30 ml of blood serum (pH 8.2.). The fiber mass samples had been treated as described in DIN 54 275. After a contact time of 60 minutes, the supernatant test liquid was centrifuged off from the sample and the pH determined using a commercially available pH-meter with a glass electrode. The effect of acidic fiber mass on the pH by comparison with normal viscose is shown in Table 3.

TABLE 3

Determination of the pH in accordance with DIN 54,275.

| Fiber Mass (3.0 g) (denier/staple length) | Serum pH for: (ml serum added) | | |
|---|---|---|---|
| | 10 ml | 15 ml | 30 ml |
| None added | 8.2 | 8.2 | 8.2 |
| Normal rayon (3.6 dtex/30 mm) | 7.88 | 8.04 | 8.17 |
| VISCOSORB 1S* (3.3 dtex/40 mm) | 4.09 | 4.30 | 4.96 |
| VISCOSORB 1N* (3.6 dtex/30 mm) | 4.30 | 4.50 | 5.44 |

*modified according to this invention

Results:

Even with 30 ml of blood serum on 3 g of fiber mass, the alkalinity of the serum can be neutralized and the pH kept near the physiological range. This demonstrates the utility of the modified fibers used in this invention for topical cosmetic and pharmaceutical purposes including absorbent cotton, swabs, bandages, catamenial devices, and the like.

DESCRIPTION OF THE PRODUCTS ACCORDING TO THIS INVENTION

The above described fibers, usually in the form of homogeneous fiber masses, may be processed by standard methods into the products of this invention. Such products include hygiene aids such as: catamenial devices including tampons, sanitary pads and napkins, and panty liners; shoe inner liners; sweat bands; and the like. Also included are cosmetic aids such as absorbent cotton batting, pads, and swabs. Further useful products are medical bandages, compresses, and the like. All of the above products, and particularly the catamenial devices, critically take advantage of the pH-regulating quality of the above-disclosed fiber. In fact, it is primarily this pH-regulating quality that critically enables the products of this invention to be distinguishable as superior to otherwise similar products.

By virtue of the low degree of substitution after conversion of the carboxyalkylate group into its free acid form, the absorption capacity and absorption rate of the materials correspond to those of normal native or regenerated cellulose or cotton. Vaginal damage through drying out due to excessive absorbency has not been observed. The colposcopic examination of women before and after the empolyment of tampons in which the pH-regulating materials are used did not reveal any damage or adverse effects.

Since the modification, i.e. etherification, is carried out on the actual cellulose raw material before production of the fiber, so that the carboxyl groups are distributed throughout the fiber cross-section, the pH-regulating materials have a distinctly better buffer capacity than materials modified after production of the fiber. Thus, where the materials are used in menstruation tampons, an acidic pH is established and maintained in use. At vaginal pH values of around 5.0, this pH helps maintain normal physiological conditions. By contrast, where conventional tampons are used, the pH is changed to a physiologically abnormal neutral to alkaline range.

After the employment of tampons in which acidic fiber materials according to the invention are used, the vaginal pH measures between 4.0 and 5.0 as opposed to a value of 6.0 to 7.0 measured after the use of conventional tampons using state-of-the-art materials. Moreover, any increase in the pH beyond the physiological limit of about 4.5 promotes bacterial growth and fungal infestation atypical of the vaginal flora. In cases of predisposition to vaginal infections, such infections recur particularly easily, especially after menstruation, because of the increased pH. This situation is distinctly improved by employing tampons in whose production pH-regulating materials are used.

In addition, any increase in the pH to beyond about 5 adversely affects the conditions for the growth of *Lactobacillus acidophilus*, which produces lactic acid, so important to a healthy vaginal environment. Accordingly, the reduction in the pH during or after the use of tampons according to the invention creates favorable starting conditions needed for a healthy vaginal environment.

In addition, the decomposition by bacteria of excreted body fluids, such as menstrual blood, and the resulting odor development is greatly retarded by using the pH-regulating materials according to this invention, as compared with conventional materials. The reason for this is that the growth of the bacteria responsible for the decomposition process is inhibited by the physiological, slightly acidic pH. It is this bacterial inhibition that also makes products using the pH-regulating materials described above useful as deodorant sweat bands, deodorant shoe pads, etc. Of course, the prevention of undesireable bacterial growth also makes the bandages, cosmetic cotton, etc., of this invention particularly useful.

This invention is further illustrated by Examples 4-9 and Table 4. All use materials in accordance with Examples 1-3 unless otherwise noted.

EXAMPLE 4

Production of tampons using pH-regulating material

Following the standard procedure for tampon manufacture, the pH-regulating fiber mass was opened up on a card and converted into cotton webbing weighing approximately 630 g per square meter. The cotton webbing was consolidated by needle punching.

The recovery cord was sewn longitudinally onto the lengths (40×90 mm) of cotton web. Compression was carried out in the axial and radial directions using the Tampax process after conditioning in a conditioning cabinet (20° C./65% relative air humidity). All the cotton fiber masses tested could be processed without difficulty and produced very good tampons.

The acidic cotton webbing showed better compressibility than conventional cotton webbing, so that tampons of slightly greater density were obtained under the same production conditions.

Using these materials, tampons and other hygiene aids may also be produced by other processes.

EXAMPLE 5

Determination of the absorption capacity of the produced tampons

The test for determining absorption capacity was carried out in an artificial vagina (Syngina) which consists of a plastic tube (internal diameter 35 mm) in which an elastic film is fitted under tension. After the tampon has been inserted, a specific pressure, for example 30 or 20 mbar, is built up with compressed air between the tube wall and the film. As a result, the film closely surrounds the tampon.

Colored test liquid is than applied from a measuring burette at a drip rate of approximately 3.5 to 4.0 ml/minute until the first drop has penetrated through to the lower end of the tampon. The quantity of liquid absorbed by the tampon is read off from the burette. The measurement can be carried out either under isobaric conditions or with increasing pressure (swelling of the tampon). The test conditions, the geometric parameters of the tampons and also the test results are shown in Tables 4A and 4B.

The dimensions and weight of the tampons were determined for the purpose of calculating the specific absorption capacity in ml/g of cotton webbing.

TABLE 4A

Dimensions and absorption capacity of tampons (Water Test)

| WATER | Test Liquid: | | |
|---|---|---|---|
| | DANUFIL product of Hoechst Co. Germany | VISCOSORB 1N (modified according to this invention) | VISCOSORB 1S (modified according to this invention) |
| Weight of cotton fiber mass (g) | 2.34 | 2.35 | 2.35 |
| Length (mm) | 38.24 | 35.78 | 36.46 |
| Diameter (mm) | 12.11 | 12.13 | 12.10 |
| Volume (ml) | 4.41 | 4.14 | 4.19 |
| Density (g/ml) | 0.531 | 0.568 | 0.561 |
| Absorption (ml/tampon) | 7.22 | 6.80 | 6.76 |
| Absorption (ml/g of cotton fiber mass) | 3.09 | 2.89 | 2.88 |

TABLE 4B

Dimensions and absorption capacity of tampons (Serum Test)

| SERUM | Test Liquid: | | |
|---|---|---|---|
| | DANUFIL product of Hoechst Co. Germany | VISCOSORB 1N (modified according to this invention) | VISCOSORB 1S (modified according to this invention) |
| Weight of cotton fiber mass (g) | 2.33 | 2.33 | 2.33 |
| Length (mm) | 38.08 | 34.98 | 35.98 |
| Diameter (mm) | 12.09 | 12.15 | 12.06 |
| Volume (ml) | 4.38 | 4.07 | 4.11 |
| Density (g/ml) | 0.532 | 0.572 | 0.567 |
| Absorption (ml/tampon) | 7.76 | 7.46 | 7.46 |
| Absorption (ml/g of cotton fiber mass) | 3.33 | 3.20 | 3.20 |

Analysis:

The absorbency of the tampons of acidic cotton fiber mass is largely comparable with that of tampons of standard absorbent cotton webbing. The slight reduction in the size of the tampons of the acidic materials results from the slightly higher density of those tampons because the compressibility of the materials is somewhat better than that of conventional cotton webbing for the same production conditions.

EXAMPLE 6

Effect of acidic cotton fiber mass on the decomposition of menstrual blood and resulting odor development Menstrual blood (3-17 ml) was collected from the vaginas of 11 different test subjects.

Quantities of 1.0 ml of menstrual blood were taken up by cotton fiber mass (250 ml) in test tubes and incubated at 37° C. An assessment of odor was made by 5 people after various times (0-8h).

Results

Compared with conventional cotton webbing, the acid cotton webbing used in this invention showed distinct inhibition of odor development which was more pronounced with modified VISCOSORB 1S than with modified VISCOSORB 1N.

EXAMPLE 7

In vivo test for physiological compatibility 25 women each used 10 tampons for one menstrual cycle, the tampons being worn for up to 12 hours. The women were colposcopically examined, particularly for vaginal irritations, before and immediately after the test period. In no case were the tampons found to produce an adverse effect. The subjective assessment of the tampons by the test subjects was also positive. No side effects were observed.

EXAMPLE 8

Measurement of the vaginal pH after employment of tampons using pH-regulating materials according to this invention The vaginal pH of the test subjects was measured using a vaginal electrode (Dr. W. Ingold KG) before and after the employment of tampons made of acidic and normal cotton fiber masses. On average, a reduction in the pH of about 1 to 2 units was observed, specifically from pH values of 6.0 to 7.0 after the use of standard tampons to physiological values of 4.0 to 5.0 after the use of tampons of acidic cotton fiber masses according to the invention.

EXAMPLE 9 pH of tampons after absorption of menstrual blood

For a test quantity of approximately 1 ml of menstrual blood per 0.25 g of cotton fiber mass, the average pH of the tampon material was 5.0 using acidified VISCOSORB 1S and 5.5 using acidified VISCOSORB 1N as compared with an average pH of 7.1 using a normal cotton fiber mass. The values were measured on tampons of 8 different test subjects.

This indicates that, after the absorption of menstrual blood, the tampon pH of an acidic cotton fiber mass according to this invention is lower by approximately 2 units than that of a conventional cotton fiber mass.

Other Products According To This Invention include catamenial devices such as sanitary pads or napkins and panty liners in which the acidic modified fiber mass is the operative body contact portion, usually confined by a porous inner side liner and nonporous outer side liner. For hygienic devices such as deodorant/antibacterial shoe liners or pads, and sweat bands or sweat pads including dress shields, the acidic modified fiber mass should be in operative body contact, usually protected by a porous layer of some other material on the body contact side. Absorbent cotton produced from the inventive acidic modified cotton is useful per se for cosmetic, first aid, and medical purposes in the usual manner. Acidic modified absorbent cotton will help maintain an acid environment in wounds, skin irritations, and the like, and may prevent the growth of physiologically abnormal microorganisms. Cotton swabs may also be manufactured from the acidic modified cotton of this invention. Bandages such as adhesive bandages, compresses, and the like, which incorporate the inventive acid modified fibers within that portion which contacts the skin, optionally separated by a porous layer, may promote healing by providing an acid environment less hospitable towards the growth of many microorganisms.

Many other uses for the inventive acidic modified cellulose fiber mass are possible, and such uses are also included in this invention. Thus, non-physiological uses for pH-regulation, as well as other unspecified physiological uses will be apparent, and are also within the scope of this invention.

We claim:

1. A hygenic pH-regulating product for topical application operatively comprising a homogeneous mass of carboxy-$C_{1-3}$-alkyl modified celluose homogeneous fibers, wherein about 1 to 30 carboxyalkyl groups are present per 100 anhydroglucose units and wherein the carboxyalkyl groups consist essentially of carboxyalkyl groups in the free acid form, wherein said carboxyalkyl groups are distributed throughout the length and diameter of the fibers.

2. The hygienic product of claim 1 wherein said fiber mass has and can maintain for some time a pH below 6 during use.

3. The hygienic product of claim 1 wherein said fiber mass has and can maintain a pH of about 4 to 5 during use.

4. The hygienic product of claim 1 wherein said product is a catamenial device.

5. The hygienic product of claim 2 wherein said product is a catamenial device.

6. The hygienic product of claim 5 wherein said device is a tampon substantially comprising said pH-regulating fiber mass.

7. The hygienic product of claim 6 wherein said device is a sanitary napkin or pad, whose operative body contact portion substantially comprises said pH-regulating fiber mass.

8. The hygienic product of claim 6 wherein said device is a panty liner whose operative body contact portion substantially comprises said pH-regulating fiber mass.

9. The hygienic product of claim 2 wherein said product is a bandage or compress whose operative body contact portion substantially comprises said pH-regulating fiber mass.

10. The hygienic product of claim 2 wherein said product is a cotton swab whose operative body contact portion substantially comprises said pH-regulating fiber mass.

11. The hygienic product of claim 2 wherein said product is absorbent cotton.

12. A hygienic shoe inner sole insert product whose operative body contact portion comprises a pH regulating homogeneous mass of carboxy-$C_{1-3}$-alkyl modified cellulose homogenous fibers, wherein about 1 to 30 carboxyalkyl groups are present per 100 anhydroglucose units and wherein the carboxyalkyl groups consist essentially of carboxyalkyl groups in the free acid form, wherein said carboxylalkyl groups are distributed throughout the length and diameter of the fibers.

13. A hygienic sweatband product whose operative body contact portion comprises a pH regulating homogeneous mass of carboxy-$C_{1-3}$-alkyl modified cellulose homogeneous fibers, wherein about 1 to 30 carboxyalkyl groups are present per 100 anhydroglucose units and wherein the carboxyalkyl groups consist essentially of carboxyalkyl groups in the free acid form, wherein said carboxylalkyl groups are distributed throughout the length and diameter of the fibers.

* * * * *